(12) United States Patent
Salpekar et al.

(10) Patent No.: US 6,699,435 B2
(45) Date of Patent: *Mar. 2, 2004

(54) CONTACT LENS PACKING SOLUTIONS

(75) Inventors: Anil Salpekar, Jamestown, NC (US); Stephen Ronald Tonge, Acocks Green (GB)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/198,819

(22) Filed: Jul. 18, 2002

(65) Prior Publication Data

US 2003/0109390 A1 Jun. 12, 2003

Related U.S. Application Data

(63) Continuation of application No. 09/445,003, filed as application No. PCT/GB98/01657 on Jun. 5, 1998, now Pat. No. 6,440,366.

(30) Foreign Application Priority Data

Jun. 6, 1997 (GB) .............................................. 9711818

(51) Int. Cl.$^7$ .......................... A61L 12/04; A61L 12/14
(52) U.S. Cl. .............................. 422/40; 422/25; 422/28; 422/34; 422/37; 422/261; 422/905; 206/205; 206/5.1; 206/316.1; 206/484; 510/112; 510/115; 134/42
(58) Field of Search .............................. 422/40, 25, 28, 422/34, 37, 261, 905; 206/205, 5.1, 316.1, 484; 510/112, 115; 134/42

(56) References Cited

U.S. PATENT DOCUMENTS

| 4,440,662 A | 4/1984 | Tsuzuki et al. ............. 252/106 |
| 4,691,820 A | 9/1987 | Martinez ..................... 206/205 |
| 4,786,436 A | 11/1988 | Ogunbiyi et al. ........... 252/352 |
| 4,820,352 A | 4/1989 | Riedhammer et al. ........ 134/30 |
| 5,209,865 A | 5/1993 | Winterton et al. ..... 252/174.22 |
| 5,704,468 A | 1/1998 | Lust et al. ................... 206/5.1 |
| 6,096,138 A * | 8/2000 | Heiler et al. ................... 134/42 |
| 6,440,366 B1 * | 8/2002 | Salpekar et al. .............. 422/40 |

FOREIGN PATENT DOCUMENTS

| EP | 0439429 | 7/1991 | ............ C11D/1/00 |
| EP | WO 98/55155 | * 12/1998 | ............ A61L/2/00 |
| WO | WO 97/20019 | 6/1997 | ............ C11D/3/00 |

* cited by examiner

Primary Examiner—Brian P. Mruk
(74) Attorney, Agent, or Firm—John E. Thomas

(57) ABSTRACT

The present invention is directed to new and improved solutions for packaging contact lenses and to methods for treating contact lenses with such solutions to improve the comfort of the lenses during wear. In particular, the present invention is directed to packing solutions comprising certain non-ionic surfactants containing a poly(oxyalkylene) copolymer and having a molecular weight of 4000 to 30,000. Such surfactants are retained on the surface of an unused lens for extended periods of time, resulting in surface modification that persists in the eye, thereby providing significant improvement in the wetting properties of fresh contact lenses used for the first time and, moreover, even several hours after lens insertion, preventing dryness and improving lubricity.

17 Claims, 5 Drawing Sheets

CONTACT LENS PACKING SOLUTIONS

This application is a Continuation of Ser. No. 09/445,003, filed on Feb. 22, 2000, now U.S. Pat. No. 6,440,366.

FIELD OF THE INVENTION

This invention relates to new and improved solutions for packaging high-water soft contact lenses and to methods for treating contact lenses with such solutions to improve the comfort of the lenses during wear. In particular, the present invention is directed to contact-lens packing solutions comprising a non-ionic surfactant that is a compound comprising at least about 90 weight percent of poly(oxyethylene) and poly(oxypropylene) segments, in one or more copolymer chains, wherein the weight average molecular weight of said surfactant is from about 4000 to about 30,000 and wherein at least about 40 weight percent of said poly(oxyethylene) and poly(oxypropylene) segments are poly(oxyethylene) segments.

BACKGROUND OF THE INVENTION

Blister-packs and glass vials are used to individually package each soft contact lens for sale to the customer. Saline or deionized water is commonly used to store the lens in the blister-packs, as mentioned in various patents related to the packaging or manufacturing of contact lenses. Because lens material may tend to stick to itself and to the lens package, packaging solutions for blister-packs have sometimes been formulated to reduce or eliminate lens folding and sticking. For this reason, polyvinyl alcohol (PVA) has been used in contact-lens packaging solutions.

The amphoteric surfactant miranol, disodium cocoamphodiacetate, has been used in a packaging solution for one-day disposable lenses, as disclosed in PCT/GB 96/02937 (GB Appln. No. 9524452.1). This application states that such a surfactant in the contact lens packet provides improved wearer comfort and avoids the inconvenience of purchasing and administering special ocular lubricants, for example, in the form of eye drops. The application, however, provides no evidence of the alleged benefits of using the compound and, for the most part, makers of contact lenses have not used any surfactants in storage solutions for new lenses.

Poloxamine and poloxamers are examples of non-ionic surfactants having one or more poly(oxyalkylene) chains. Poloxamines and poloxamaers are well-known wetting and lubricating agents for contact lenses and have been used in lens wetting drops and in lens-care solutions for treating lenses after use or while in use in the eye. For example, U.S. Pat. No. 4,786,436 and several other patents to Ogunbiyi et al. disclose poloxamine as a wetting agent. Contact-lens rewetting drops containing surfactants such as poloxamine and poloxamer have been used to make contact lens wear more comfortable, to soothe the eyes, and to moisten lenses to minimize dryness. Surfactants such as poloxamine, poloxamer, and tyloxapol have been used in multi-purpose solutions, for cleaning, wetting, and storing lenses.

Certain combinations of poly(oxyalkylene) surfactants have also been disclosed for use in the eye to preventively clean lenses and inhibit deposits. For example, U.S. Pat. No. 5,209,865 (Winterton et al.) discloses the combination of certain poloxamers and poloxamines to maintain clean lenses in the eye.

Work presented by Lyndon Jones at the 1995 BCLA (British Contact Lens Association) Conference has indicated that patients who use a ReNu® multi-purpose solution for cleaning, storing, and wetting lenses experienced increased comfort with lenses worn over short wearing times of 2–4 weeks when compared to other solutions. ReNu® solution comprises a borate buffered isotonic solution having several unique aspects, including the combination of a borate buffer, a PHMB disinfecting agent, and a poloxamine surfactant at specified concentrations.

Non-ionic surfactants, including poloxamine and poloxamer compounds, have not been used for wetting fresh or unused lenses. This is probably largely due to the widespread belief that tear fluid provides adequate wetting for fresh or unused contact lenses, and that any surfactant on the lens would be quickly displaced in the eye. Fresh lenses in FDA categories Group II or Group IV contain at least fifty percent water content and are expected to be well hydrated when taken from the blister-pack for first use.

It has been stated that if a lens is thoroughly cleaned before insertion, lacrimal fluid can adequately wet the lens. Furthermore, the difficulties of adding a surfactant to a packaging solution, including the possibility of lowering shelf-life and/or adverse reactions during heat sterilization, have further limited the use of surfactants in a packaging solution for the purpose of providing any possible or marginal effect on lens comfort. It is only after a lens has been worm, when proteins or other deposits have formed on the surface of the lens, that surfactants have been used in standard lens-care solutions.

It is highly desirable that contact lens be as comfortable as possible for wearers. Manufacturers of contact lens are continually working to improve the comfort of contact lenses. Nevertheless, many people who wear contact lenses still experience dryness or eye irritation throughout the day and particularly towards the end of the day. An insufficiently wetted lens at any point in time will cause significant discomfort to the lens wearer. Although wetting drops can be used as needed to alleviate such discomfort, it would certainly be desirable if such discomfort did not arise in the first place.

BRIEF DESCRIPTION OF THE INVENTION

Figure 1:
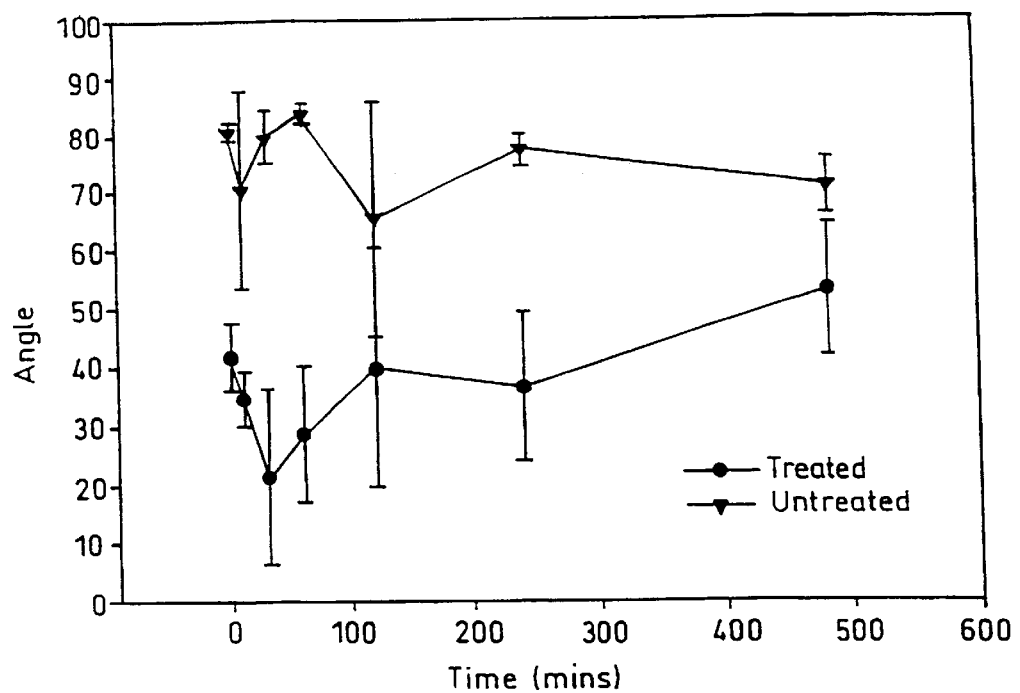
FIG. 1 shows the advancing angles for fresh contact lenses from a poloxamine-containing packing solution, compared to fresh contact lenses from a conventional saline packing solution over a period of 8 hours.

This invention relates to new and improved solutions for packaging contact lenses and to methods for treating contact lenses with such solutions to improve the comfort of the lenses during wear. In particular, the present invention is directed to packing solutions comprising certain non-ionic surfactants that is a compound comprising at least 90 weight percent of poly(oxyethylene) and poly(oxypropylene) segments, in one or more copolymer chains, wherein the weight average molecular weight of said surfactant is from about 4000 to about 30,000 and wherein at least about 40 percent of said copolymer poly(oxyethylene) and poly(oxypropylene) segments are poly(oxyethylene) segments.

The gist of the invention is based on the discovery that a certain class of poly(oxyethylene)-poly(oxypropylene) surfactants are retained on the surface of an unused lens, resulting in surface modification of the lens that surprisingly persists in the eye for an extended period of time. Such surfactants can provide a significant improvement in the wetting properties and comfort of fresh contact lenses used for the first time. Even several hours after lens insertion, such poloxamine surfactants can prevent or eliminate lens unwetting in the eye and improve lens lubricity.

In accordance with the invention, a sterile ophthalmically safe aqueous storage solution is used for packaging contact lenses, which solution has a pH of 6 to 8 and comprises from about 0.005 to about 5.0 weight percent, preferably 0.01 to 1.0 weight percent, of a non-ionic or neutral surfactant selected from the group consisting of soluble and non-toxic poloxamines having a weight average molecular weight of about 4,000 to 30,000, preferably 5,000 to 25,000, and most preferably 7,500 to 15,000.

The solution also contains at least one tonicity adjusting agent, optionally in the form of a buffering agent, for providing an isotonic or close to isotonic solution such that the osmolality of about 200 to 400 mOsm/kg, preferably 250 to 350 mOsm/kg. The solution is typically sterilized by heat and hermetically sealed. The solution, therefore, may be used in the absence of a germicide compound.

The invention is also directed to a method for packaging and storing a high water (FDA Group II or Group IV) contact lens comprising immersing the contact lens in the above-described aqueous contact-lens solution inside a package prior to delivery to the customer-wearer. Finally, the invention is also directed to a system for the storage and delivery of a contact lens comprising a sealed container containing one or more unused contact lens immersed in the above-described aqueous contact-lens packaging solution. Typically, the sealed container is a hermetically sealed blister-pack, in which a concave well containing a contact lens is covered by a metal or plastic sheet adapted for peeling to open the blister-pack.

DETAILED DESCRIPTION OF THE INVENTION

Generally, contact lenses in wide use fall into two categories: (1) the hard or rigid gas permeable corneal type lenses formed from materials prepared by polymerization of acrylic esters, such as polymethyl methacrylate (PMMA), silicone acrylates and fluorosilicone methacrylates and (2) gel, hydrogel or soft type lenses are formulated from polymers having a proportion of hydrophilic repeat units derived from monomers such as 2-hydroxyethyl methacrylate (HEMA) or other hydrophilic monomers such that the water content of the lens during use is at least 20% by weight. The term "soft contact lens" generally refers to those contact lenses which readily flex under small amounts of force and return to their original shape when that force is released.

The present invention is intended for use in connection with relatively high-water soft lenses having at least about 50 percent (by weight) water content (hereafter "high-water lenses"). The present invention is especially useful with respect to hydrophilic lenses made from polymers having repeats units derived from hydroxyethyl methacrylate monomers, and especially lenses made from polymers having additional repeat units derived from methacrylic acid or NVP (N-vinylpyrrolidone). In general, the invention is applicable to ionic or non-ionic lenses in U.S. FDA category Group II and IV. Group IV lenses often contain repeat units derived from methacrylic acid monomers. Group IV is distinguished from Groups I to III by having (with respect to Group I and III) higher water content and (with respect to Group I and II) being more ionic.

Group II and Group IV lenses have a water content greater than 50% by weight, preferably about 55% to 80% water. High water content is associated with materials having high oxygen permeability, resulting in the increasing popularity of such lenses, including especially disposable and planned-replacement lenses. Group IV materials include, but are not limited to, bufilcon A, etafilcon A, methafilcon A, ocufilcon C, perfilcon A, phemfilcon A, and vifilcon A. Materials containing methacrylic acid monomers include methafilcon B, ocufilcon D, methafilcon A, and etafilcon A (USAN and the USAP Dictionary of Drug Names). Group II materials include, by way of example only, lidofilcon A or B, alphafilcon A, Sauflon, Hydron, etc., which materials typically contain primarily HEMA and NVP (N-vinylpyrrolidone). DMA (N,N-dimethylacrylamide) is another Group II monomer that may be used in Group II lens materials to provide hydrophilicity.

Lenses made from the foregoing materials are commercially available from a variety of sources. Such lenses include daily-wear lenses, extended-wear lenses, planned-replacement lenses, and disposable lenses.

By the term "disinfecting agent" herein is meant a microbicidal compound that is effective for reducing or substantially eliminating the presence of an array of microorganisms present in a contact lens, which can be tested by challenging a contact lens with a specified innoculum of such microorganism. An effective amount of disinfecting agent is an amount which will at least partially reduce the microorganism population in the formulations employed, specifically a disinfecting amount is that which will reduce the microbial burden by two log orders in four hours and more preferably by one log order in one hour (without rubbing), in accordance with the FDA Chemical Disinfection Efficacy Test—July, 1985 Contact Lens Solution Draft Guidelines. In the preferred embodiment of a packing solution according to the present invention, the solution is heat sterilized and packaged for sale in the absence of a effective amount of disinfecting agent.

The packaging solutions according to the present invention are physiologically compatible. Specifically, the solution must be "ophthalmically safe" for use with a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and comprises materials, and amounts thereof, that are non-cytotoxic according to ISO standards and U.S. FDA (Food & Drug Administration) regulations. The solution should be sterile in that the absence of microbial contaminants in the product prior to release must be statistically demonstrated to the degree necessary for such products.

As indicated above, the present solution comprises anonionic surfactant that has been found unexpectedly effective as a comfort agent for treating unused lenses, whereby the comfort agent is released by the lens over an extended period of time. The comfort agent is suitably employed in amounts ranging from 0.005 to 5.0 percent, preferably 0.01 to 1.0 percent by weight of the composition or solution. The surfactant should be soluble in the lens care solution, not become turbid, and should be non-irritating to eye tissues. The surfactant comprises at least about 90 weight percent of poly(oxyethylene) and poly(oxypropylene) segments, preferably at least 95 to 100 weight percent of poly(oxyethylene) and poly(oxypropylene) segments in one or more block copolymer chains, wherein the weight average molecular weight of said surfactant is from about 4000 to about 30,000 and wherein at least about 40 percent of said segments are poly(oxyethylene) segments. A preferred surfactant, for use as a comfort agent in contact-lens packing solutions, comprises a plurality of poly(oxyalkylene) chains, each of the poly(oxyalkylene) chains comprising a block copolymer of poly(oxyethylene) and poly(oxypropylene) segments, wherein the weight average molecular weight of said surfactant is from about 7500 to about 25,000 and wherein at least about 40 percent of said chains are poly(oxyethylene). Preferably, the number of chains is 2 to 6 and may be attached to a central moiety containing one or more, preferably 1–3, nitrogen atoms. One non-ionic surfactant that has been found to be particularly advantageous consists of a poly(oxypropylene)-poly(oxyethylene) adduct of ethylene diamine and has a molecular weight from about 7,500 to about 25,000 wherein at least 40 weight percent of said adduct is poly(oxyethylene). The CTFA Cosmetic Ingredient Dictionary's adopted name for this group of surfactants is poloxamine. Such surfactants are available from BASF Wyandotte Corp., Wyandotte, Mich., under the registered trademark "Tetronic". Examples of suitable poloxamers are Pluronic® F108, F88, F68, F68LF, F127, F87, F77, P85, P75, P104, and P84. Examples of suitable poloxamines are Tetronic® 707, 1107 and 1307.

Optionally, other non-ionic surfactants may be included in the packing solution in combination with the above-described comfort agents, for example, polyethylene glycol esters of fatty acids, e.g. coconut, polysorbate, polyoxyethylene or polyoxypropylene ethers of higher alkanes ($C_{12}$–$C_{18}$). Examples include Tween® 20 (polysorbate 20) and Tween® 80, polyoxyethylene (23) lauryl ether (Brij® 35), polyoxyethyene (40) stearate (Myrj® 52), polyoxyethylene (25) propylene glycol stearate (Atlas® G 2612).

If desired, an amphoteric, cationic, or anionic surfactant may also be present in combination with the present comfort agent. Amphoteric surfactants suitable for use in a composition according to the present invention include materials of the type are offered commercially under the trade name "Miranol". Another useful class of amphoteric surfactants may be exemplified by the following chemical structure are exemplified by cocoamidopropyl betaine commercially available under the trade name Amphoso CA.

Surfactants suitable for use in the invention can be readily ascertained, in view of the foregoing description, from *McCutcheon's Detergents and Emulsifiers*, North American Edition, McCutcheon Division, MC Publishing Co., Glen Rock, N.J. 07452 and the *CTFA International Cosmetic Ingredient Handbook*, Published by The Cosmetic, Toiletry, and Fragrance Association, Washington, D.C.

In one embodiment of the present invention, a Group II or Group IV contact lens is immersed in an aqueous contact-lens solution inside a package prior to delivery to the customer-wearer, wherein the contact lens solution comprises a sterile ophthalmically safe aqueous solution comprising from about 0.005 to about 2.0 weight percent of a neutral or non-ionic surfactant as described above.

The pH of the present solutions should be maintained within the range of about 6.0 to 8.0, preferably about 6.5 to 7.8. Suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Generally, buffers will be used in amounts ranging from about 0.05 to 2.5 percent by weight, and preferably, from 0.1 to 1.5 percent. The packaging solutions of this invention preferably contain a borate buffer, containing one or more of boric acid, sodium borate, potassium tetraborate, potassium metaborate or mixtures of the same.

Typically, the aqueous solutions of the present invention for packaging and storing contact lenses are also adjusted with tonicity agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Examples of suitable tonicity adjusting agents include, but are not limited to: sodium and potassium chloride, dextrose, glycerin, calcium and magnesium chloride. These agents are typically used individually in amounts ranging from about 0.01 to 2.5% (w/v) and preferably, form about 0.2 to about 1.5% (w/v). Preferably, the tonicity agent will be employed in an amount to provide a final osmotic value of 200 to 400 mOsm/kg and more preferably between about 250 to about 350 mOsm/kg, and most preferably between about 280 to about 320 mOsm/kg.

It may also be desirable to optionally include water-soluble viscosity builders in the solutions of the present invention. Because of their demulcent effect, viscosity builders have a tendency to further enhance the lens wearer's comfort by means of a film on the lens surface cushioning impact against the eye. Included among the water-soluble viscosity builders are the polymers like polyvinylalcohol cellulose-derived polymers, and povidone. Such polymers may be used in an amount of from about 0.01 to about 4.0 weight percent or less.

In one embodiment of a method according to the present invention, the claimed solution is used to package and store a disposable or a daily disposable lens, although the present invention may also be used for planned replacement lenses (PRL) that are replaced after a period of use under 4 weeks, for example, 1 day or 2 weeks. As indicated above, such lenses can be made from a polymer comprising about 0.5 to 5 mole percent repeat units derived from methacrylic acid (MAA), 10 to 99 mole percent of repeat units derived from hydroxyethyl methacrylate, and about 0.5 to 5 mole percent of cross-linking repeat units. Cross-linking repeat units may be derived, for example, from such monomers as ethyleneglycol dimethacrylate, divinylbenzene, and trimethylpropane trimethacrylate. Alternatively, such lenses can be made from a polymer containing primarily repeat units derived from HEMA and NVP (N-vinylpyrrolidone) monomers.

The present invention is particularly advantageous where the lens packet contains a one-day lens for which the packaging solution is the only solution in which the lens will be soaked, since the lens will not be subject to further cleaning or storing after it is worn.

The method of packaging and storing a contact lens according to the present invention comprises packaging a contact lens immersed in the aqueous contact-lens packaging solution described above. Said method may comprise immersing the contact lens in an aqueous contact-lens solution prior to delivery to the customer/wearer, directly following manufacture of the contact lens. Alternately, the packaging and storing in the solution of the present invention may occur at an intermediate point before delivery to the ultimate customer (wearer) but following manufacture and transportation of the lens in a dry state, wherein the dry contact lens is hydrated by immersing the contact lens in the contact-lens packaging solution. Consequently, a package for delivery to a customer may comprise a sealed container containing one or more unused contact lenses immersed in an aqueous contact-lens packaging solution according to the present invention.

Conveniently, the non-ionic surfactant (comfort agent) is added to a conventional packing solution, for example saline or buffered saline, and mixed therewith, prior to introduction thereof into a container or blister-pack holding a contact lens, after which the container is sealed. Alternatively, the surfactant may be added directly to a conventional packing solution previously introduced into a container for the contact lens, prior to sealing of the container. The contact lens may be present in the packing solution when the comfort agent is added or introduced subsequently before sealing of the container.

In one embodiment, the steps leading to the present contact lens packaging system comprises (1) molding a contact lens in a mold comprising at least a first and second mold portion, (2) hydrating and cleaning the lens in a container comprising at least one of said mold portions, (3) introducing the packing solution with the comfort agent into the container with the lens supported therein, and (4) sealing the container. Preferably, the method also includes the step of sterilizing the contents of the container. Sterilization may take place prior to, or most conveniently after sealing of the container and may be effected by any suitable method known in the art, for example, by balanced autoclaving of the sealed container at temperatures of approximately 120° C. or above.

A system for the storage and delivery of a contact lens according to the present invention comprises a sealed container containing one or more unused Group II or Group IV contact lens immersed in the above-described aqueous contact-lens packaging solution. Preferably, the sealed container is a hermetically sealed blister-pack, in which a concave well containing a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, or the like.

The following specific experiments and examples demonstrate the compositions and methods of the present invention. However, it is to be understood that these examples are for illustrative purposes only and do not purport to be wholly definitive as to conditions and scope.

EXAMPLE 1

This example illustrates the "persistence" effect of the poloxamine comfort agent on in vivo hydrogel contact lens wettability, when worn for 8 hours and was assessed in six pre-existing soft lens wearers, using Group IV (Surevue®) lenses. Lenses pre-soaked in a poloxamine-containing packing solution, lenses soaked in saline and lenses worn for various time periods were compared. Measurements of dynamic advancing and receding contact angle were made using the DCA technique and compared to subjective patient comfort scores, attained using a standard analogue scale.

Six pre-existing soft lens wearing subjects were recruited, all of whom currently wore Surevue® Group IV contact lenses. Each subject was screened prior to the investigation commencing to ensure that no pre-existing corneal complications were present. Prior to participating in the study, patients ceased to wear their lenses for 48 hours, to prevent any disruption of the tear film.

Sufficient lenses for the study were either pre-soaked in a poloxamine-containing solution (0.1% by weight Tetronic® 1107) or saline (Alcon "Salette") for a minimum of 12 hours to condition the lens surface. Measurements of dynamic advancing and receding contact angle were made on four lenses without patient wear. This was regarded as "time 1". Lenses were inserted into subjects with sterile gloved hands (to prevent the transfer of skin lipids) as a matched pair of −3.00D lenses. Lenses were then removed with sterile, plastic-tipped tweezers and immediately examined using the dynamic contact angle apparatus.

Lenses were examined after wearing times of 10 minutes (time 2), 30 minutes (time 3), 60 minutes (time 4), 120 minutes (time 5), 240 minutes (time 6) and 480 minutes (time 7). Each eye was treated as a separate data point. Starting points were staggered such that lenses were processed immediately following removal, minimizing any disruption of the surface film developed after in-vivo wear.

Dynamic contact angle (DCA) measurement, based upon the Wilhelmy plate technique, enabled advancing and receding contact angles to be measured. In the Wilhelmy plate technique for measuring the dynamic contact angle (DCA), the solid test sample is held by an electrobalance (Whites Electrical Instruments, Malvern, England. Model No. DB 2kS) and the test solution raised or lowered on a scissor jack with motorized micropositioner (Ealing Electro-Optics, Watford, England) in order to alternately immerse the sample. The results of the experiment are expressed graphically with the x-axis representing the immersion depth and the y-axis showing the force exerted by the test sample. The force is proportional to the apparent weight of the sample, and this in turn, is defined by the height of the meniscus of liquid adhered to the sample (a product of wetting) and the buoyancy. The latter information allows the contact angle at the instant of insertion and removal from the test liquid, that is, when there are no buoyancy effects, to be calculated using the following formula:

$$\cos\Theta = \frac{F}{\gamma \times P}$$

Where:

$\Theta$ advancing or receding contact angle

F=measured force dynes

γ surface tension of test solution—dynes/cm
P=perimeter of test sample—cm

The test was conducted on fully hydrated hydrogels/lenses and the hysteresis observed between the advancing ($\Theta_A$) and receding ($\Theta_R$) contact angles was taken as an indication of the change in the level of wettability of the sample between the dry and wet state. This, in turn, is a consequence of the mobility of the groups present at the surface. In the case of an untreated hydrogel in air the polymer chains will freely rotate to orientate their hydrophobic or non-wettable moieties towards the hydrophobic air/gel interface, whilst in the wetted state the reverse will occur and the hydrophilic groups will orientate themselves towards the aqueous/gel interface.

Any surface with an absorbed layer of surfactant material, where the surfactant possesses a shell of water molecules associated with its exposed head groups will not be subject to same levels of surface mobility and will thereby exhibit a reduced hysteresis. Any treated material that shows a low $\Theta_A$ combined with a negligible hysteresis could be considered to be fully wettable and is taken as the 'gold standard' in these studies.

A sample of lens material approximately 20 mm long and 5 mm wide was cut to a uniform size using a sample cutter (Ray Ran, Nuneaton, England). The samples were taken from each of the test lenses immediately following lens removal. One end of the lens was secured to a clip and attached to the electrobalance with the addition of a lead weight and hook to maintain the lens strip in a straightened condition. All DCA measurements were assessed using HPLC grade water (FSA—Loughborough, England) as the probe liquid.

The surface tension of the probe solution (HPLC water) after repeated immersions of the test lens samples were measured with a du Nuoy ring and used as an indication of the release of surfactant from the surface of the contact lens.

The surface tension of the probe solution (HPLC water) after repeated immersions of the test lens samples were measured with a du Nuoy ring and used as an indication of the release of surfactant from the surface of the contact lens.

Statistical analysis was undertaken using conventional non-parametric techniques and data was also presented on a case-study basis. Krushal-Wallis One-Way ANOVA on Ranks, was the chosen method of analysis with SNK or Dunnets Method being employed for testing comparisons within groups which proved to be significantly different. In all cases statistical significance was taken as $p<0.05$.

FIG. 1 shows the advancing angles for fresh contact lenses from a poloxamine-containing packing solution, compared to fresh contact lenses from a conventional saline packing solution over a period of 8 hours. The data is shown Table 1 below. The results indicate that there is a significant difference between treatments at all time intervals ($p<0.001$) except after 8 hours of wear (p=NS). In treated lenses the angle is low initially and shows a gradual but progressive rise over the 8 hour wearing period. This is in contrast to the position with untreated lenses, where the advancing angle remains elevated throughout the wearing period, with no significant change occurring, although a trend towards a slight reduction in advancing angle can be seen graphically. In both of these cases the change over time is not statistically significant (p=NS). Treatment results in a statistically significant reduction in advancing angle ($p<0.001$) after all wearing periods.

The advancing angle indicates the wettability of the lens in the non-wetted state. This is the case when the surface film is absent upon initial lens insertion or when the lens becomes dewetted during wear, which is when the lens is most problematic to the patient. The poloxamine-treated lenses remain more wettable (when dry) than untreated lenses at all times over the 8 hours of wear and this is likely to be the result of a layer of adherent poloxamine comfort agent. Untreated lenses are not significantly modified by the tear film over this time period.

TABLE 1

| | Advancing Angles | | | | | | |
|---|---|---|---|---|---|---|---|
| | Time | | | | | | |
| | 0 mins | 10 mins | 30 mins | 60 mins | 120 mins | 240 mins | 480 mins |
| Treated | 41.6 ± 5.6 | 34.6 ± 4.6 | 21.2 ± 15.1 | 28.5 ± 11.4 | 39.8 ± 20.4 | 36.4 ± 12.7 | 53.0 ± 11.4 |
| Untreated | 80.5 ± 1.6 | 70.4 ± 17.1 | 79.4 ± 4.6 | 83.4 ± 1.8 | 65.2 ± 20.3 | 77.1 ± 2.9 | 70.7 ± 4.8 |

Figure 2:
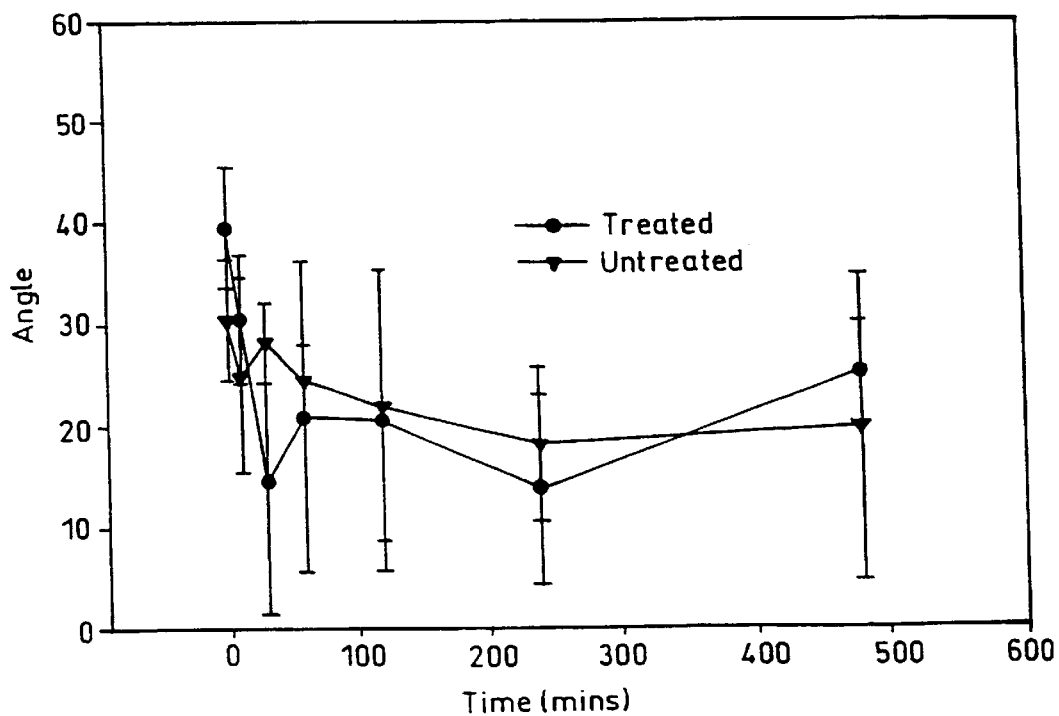
FIG. 2 shows the receding angles for fresh contact lenses from a poloxamine-containing packing solution, compared to fresh contact lenses from a conventional saline packing solution over a period of 8 hours.

FIG. 2 shows the receding angles for fresh contact lenses from a poloxamine-containing packing solution, compared to fresh contact lenses from a conventional saline packing solution over a period of 8 hours. The data is shown in Table 2 below. In the case of the receding angles, no significant differences were found between treated and untreated lenses (p=NS). Results show that both treated and untreated lenses remain equally wettable when in the wet state. Although not statistically significant between treatments, there is a clear trend for ReNu treated lenses to be more wettable (when wet) than untreated lenses at all time intervals, except at the 8 hour reading. This trend is particularly apparent over the initial 30 minutes of wear. There is also a trend indicating an initial increase in wettability for both lens groups. There are no statistically significant effects between treatments, but there is a change in both treated and untreated materials over time, with post-hoc testing indicating that this difference is significant between the initial and final readings ($p<0.02$).

The lack of difference between the treated and untreated lenses indicates that in the wetted state both lens groups are equally wettable. This is not surprising, since wetted hydrogel surfaces are not clinically problematic because they retain a surface tear film coating.

TABLE 2

Receding Angles

| | Time | | | | | | |
|---|---|---|---|---|---|---|---|
| | 0 mins | 10 mins | 30 mins | 60 mins | 120 mins | 240 mins | 480 mins |
| Treated | 39.4 ± 5.9 | 30.4 ± −6.2 | 14.5 ± 13.1 | 20.8 ± 15.2 | 20.5 ± 14.7 | 13.6 ± 9.3 | 25.0 ± 5.1 |
| Untreated | 30.4 ± −5.9 | 24.9 ± 9.6 | 28.1 ± 3.9 | 24.5 ± 3.4 | 21.8 ± 13.2 | 18.1 ± 7.6 | 19.6 ± 15.0 |

Figure 3:
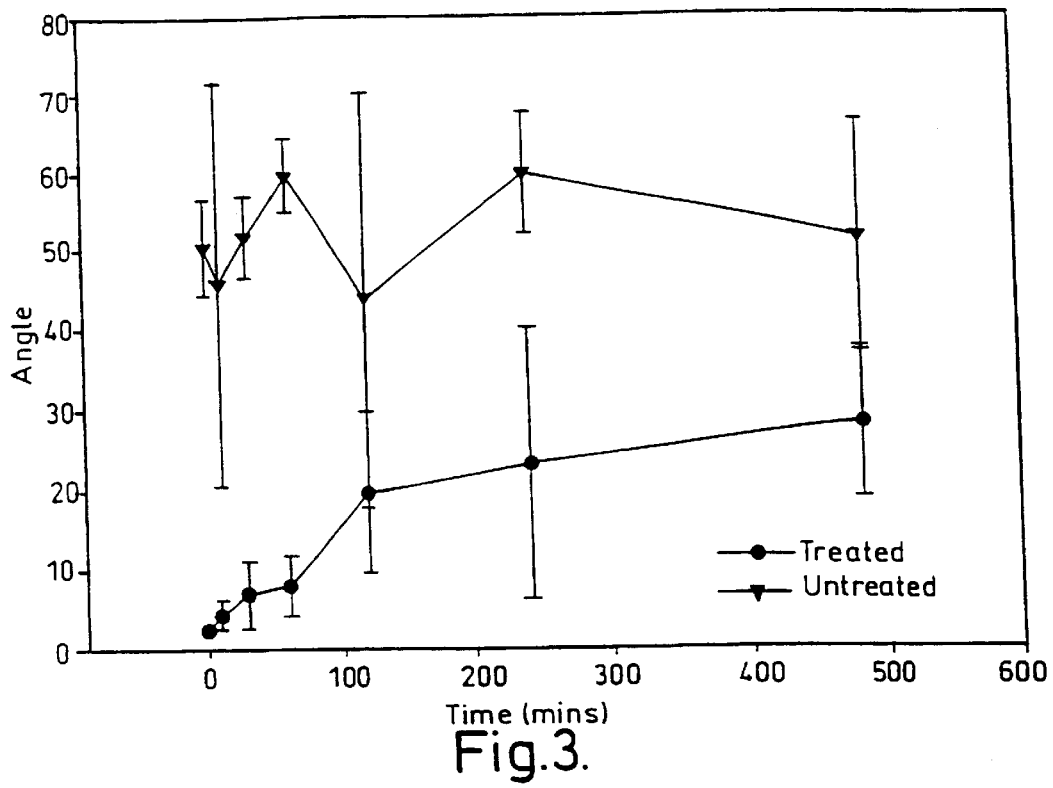
FIG. 3 shows the contact-angle hysteresis for fresh contact lenses soaked in a poloxamine-containing packing solution compared to fresh contact lenses from a conventional saline packing solution over a period of 8 hours.

FIG. 3 shows the contact-angle hysteresis for angles for fresh contact lenses soaked in a poloxamine-containing packing solution compared to fresh contact lenses from a conventional saline packing solution over a period of 8 hours. The data is shown in Table 3 below. These are the most striking results and clearly show that the poloxamine treated fresh lenses exhibit a low hysteresis value over the first 60 minutes of wear, between 60 and 120 minutes the hysteresis values shows a marked increase and then a gradual increase over the next 6 hours of wear. However, even after 8 hours of wear the hysteresis remains lower than that exhibited by untreated lenses after any period of wear. The effect of treatment is statistically significant at all time periods ($p<0.001$).

These results indicate that the surface mobility in the treated lenses remains reduced as a result of the presence of adherent poloxamine comfort agent at the surface over 8 hours of wear, compared to untreated lenses, which retain a high level of surface mobility over 8 hours of wear. Surprisingly, this shows that the surface of FDA Group IV lenses does not become modified by components within the tear film as a result of wear.

period of 8 hours. The data is shown in Table 4 below. A significant difference was noted between the surface tension values of treated and untreated lenses ($p<0.001$). Multiple testing indicated that these differences were significant ($p<0.05$) at all time periods except 120 and 480 minutes. However, even at these intervals the probe fluid surface tension remained lower in treated lenses when compared with untreated lenses. In untreated lenses there are no statistically significant differences over time (p=NS), while in treated lenses there is a statistically significant change across time between the initial and all subsequent times ($p<0.05$).

These results suggest that surface active material from the treated lenses is rapidly lost over the first 2 hours of wear then slowly lost over the remaining 6 hours. This agrees with the hysteresis data and shows that even after 8 hours of wear, when the surface tension of the probe liquid is not significantly different to that of probe water from untreated lenses, the surface of the lenses is still modified, i.e. the adherent surfactant material remains attached so as to modify the

TABLE 3

Hysteresis

| | Time | | | | | | |
|---|---|---|---|---|---|---|---|
| | 0 mins | 10 mins | 30 mins | 60 mins | 120 mins | 240 mins | 480 mins |
| Treated | 2.2 ± 0.6 | 4.2 ± 1.8 | 6.7 ± 4.2 | 7.7 ± 3.8 | 19.3 ± 10.0 | 22.8 ± 16.8 | 28.0 ± 9.0 |
| Untreated | 50.1 ± 6.1 | 45.5 ± 25.3 | 51.3 ± 5.2 | 59.0 ± 4.7 | 43.4 ± 25.9 | 59.1 ± 7.6 | 51.1 ± 14.5 |

Figure 4:
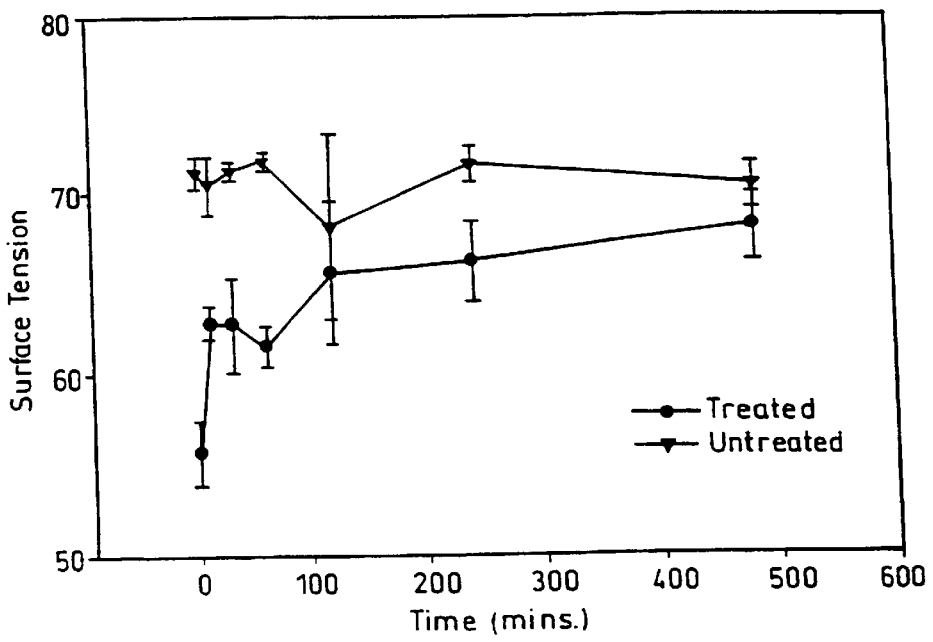
FIG. 4 shows the surface tension of probe liquid after lens immersion for fresh contact lenses soaked in a poloxamine-containing packing solution compared to fresh contact lenses from a conventional saline packing solution over a period of 8 hours.

FIG. 4 shows the surface tension of probe liquid after lens immersion for fresh contact lenses soaked in a poloxamine-containing packing solution compared to fresh contact lenses from a conventional saline packing solution over a surface of the lenses but is not easily removed into the probe solution. At this stage it is likely that only a thin layer of surfactant remains, although this is sufficient to retain a degree of surface modification.

TABLE 4

Surface Tension of Probe Liquid

| | Time | | | | | | |
|---|---|---|---|---|---|---|---|
| | 0 mins | 10 mins | 30 mins | 60 mins | 120 mins | 240 mins | 480 mins |
| Treated | 55.7 ± 1.8 | 62.8 ± 0.9 | 62.7 ± 2.6 | 61.5 ± 1.1 | 65.5 ± 3.9 | 66.1 ± 2.2 | 68.0 ± 1.9 |
| Untreated | 71.0 ± 0.9 | 70.3 ± 1.6 | 71.1 ± 0.5 | 71.6 ± 0.5 | 68.0 ± 5.1 | 71.5 ± 1.0 | 70.3 ± 1.3 |

The equilibrium water content (EWC) was measured for each lens to observe the effect of hydration on lens wettability and comfort. The EWC are given in Table 5 below. Statistical analysis shows that there are no differences between treated and untreated lenses, and hence, the wettability effects observed are due to surfactant treatment rather than lens dehydration. A significant dehydration of lenses occurred immediately upon insertion into the eye but a further progressive dehydration was not observed.

TABLE 5

Equilibrium Water Content

| Time | 0 mins | 120 mins | 240 mins | 480 mins |
|---|---|---|---|---|
| Treated | 58.3 ± 0.5 | 55.8 ± 0.8 | 55.0 ± 1.6 | 54.3 ± 1.9 |
| Untreated | 58.3 ± 0.5 | 56.0 ± 0.7 | 55.3 ± 0.8 | 54.3 ± 0.8 |

In summary of the above, the poloxamine-containing solution results in a significant improvement in surface wetting of Group IV lenses and this enhanced wettability is retained for a period of at least 8 hours of in-eye wear. The enhanced wettability noted over the 8 hour wearing period in lenses treated with poloxamine results from the retention of surfactant on the surface of the lens rather than deposition of ocular mucin over the wearing period. Measurements of the surface tension of the probe solution indicated that surfactant material was released from poloxamine treated lenses after 6 hours of lens wear.

COMPARATIVE EXAMPLE 2

This Example illustrates that whereas, as shown in Example 1 above, a defined amount of poloxamine comfort agent contained in a packing solution appears to remain adhered to the surface of Surevue® lenses up to one hour post-insertion, surface active components within the tear film do not modify the surface properties of Surevue® lenses. The influence of native ocular surfactants on the wettability of FDA group IV hydrogel contact lenses when worn for various time periods was investigated as follows. Six pre-existing soft lens wearing subjects were recruited, all of whom currently wore Surevue® lenses. Prior to this study, the patients ceased to wear their lenses for 48 hours, to prevent any disruption of the tear film. Each subject was screened prior to the investigation commencing to ensure that no pre-existing corneal complications were present.

Four lenses were rinsed in saline and then soaked for at least at least 24 hours in saline. These were used for control measurements and were designated as "saline treated lenses." Study lenses were rinsed in non-preserved saline and then soaked in the same solution for at least 24 hours prior to commencing the study. This ensured that any packaging solution was thoroughly rinsed from the lenses prior to wear. Lenses were examined after wearing times of 10 minutes (Time 1), 30 minutes (Time 2) and 60 minutes (Time 3). Each eye was treated as a separate data point. This provided 4 measurements for each sampling time from four subjects. Starting points were staggered such that lenses were processed immediately following removal, minimizing any disruption of the surface film developed after in-vivo wear.

Dynamic contact angle (DCA) measurement, based upon the Wilhelmy plate technique, enabled advancing and receding contact angles to be measured by dipping a section of a test contact lens into a standard solution. A sample of lens material approximately 10 mm long and 3–4 mm wide was cut to a uniform size using a sample cutter (Ray Ran, Nuneaton, England). The samples were taken from each of the test lenses immediately following lens removal. One end of the lens was secured to a clip and attached to an electrobalance (Whites Electrical Instruments, Malvern, England) with the addition of a lead weight and hook to maintain the lens strip in a straightened condition. All DCA measurements were assessed using HPLC grade water (FSA—Loughborough, England) as the probe liquid.

The surface tension of the probe solution (HPLC water) after repeated immersions of the test lens samples were measured with a du Nuoy ring and used as an indication of the release of surfactant from the surface of the contact lens.

Statistical analysis was undertaken using conventional non-parametric techniques and data was also presented on a case-study basis. Krushal-Wallis One-Way ANOVA on Ranks, was the chosen method of analysis with SNK or Dunnets Method being employed for testing comparisons within groups which proved to be significantly different. In all cases statistical significance was taken as $p<0.05$.

The DCA measurements are consistent with the results for untreated lenses in Example 1 above (Tables 1, 2, and 3). Surface tension results of the probe liquid from untreated lenses are shown in Table 6 below. No significant difference was noted between the surface tension values (p=NS). This indicates that no surface active materials from the tear film adhere to the lens surface and become released into the probe liquid. Consequently, it is clear that no surface modification of the lens material occurs up to one hour post-insertion.

TABLE 6

Surface Tension of Probe Liquid

| | | | Time | | |
|---|---|---|---|---|---|
| | Saline | ReNu | 10 mins | 30 mins | 60 mins |
| Mean | 69.7 | 70.3 | 71.3 | 71.6 | 71.2 |
| SE | 0.6 | 09 | 0.3 | 0.3 | 0.6 |

In view of the above results, it is clear that surface active components within the tear film do not adhere to the surface of Surevue® Group IV lenses, and therefore do not result in a lowering of both the advancing angle and contact angle hysteresis during the first 60 minutes of lens wear. These results contrast markedly with those reported for RGP materials by other workers. Previous studies by Raheja et al. using RGP materials indicated that the surface characteristics of untreated lenses are markedly altered when placed in the eye, purportedly by the presence of surfactant materials within the tear film. (Raheja, M. K. and Ellis, E. J., "Achieving New Levels of RGP Comfort," Contact Lens Spectrum, 45–48, October 1995), indicating that such effects are likely to be highly material specific and not obvious even to one skilled in the art.

EXAMPLE 3

This example illustrates comparative surface chemical properties of various surfactants for use in a contact-lens packing solution, including the persistence thereof. The following surfactants were tested: Pluronic® F127 (a poloxamer), Tetronic 1107 (a poloxamine), and tyloxapol. (Tyloxapol is a non-ionic surfactant that is an oxyethylated tertiary octylphenol formaldehyde polymer.) The test was conducted on fully hydrated hydrogels/lenses and the hysteresis observed between the advancing and receding contact angles was taken as an indication of the change in the level of wettability of the sample between the dry and wet state. This, in turn, is a consequence of the mobility of the groups present at the surface. In the case of an untreated hydrogel in air the polymer chains will freely rotate to orientate their hydrophobic or non-wettable moieties towards the hydrophobic air/gel interface, whilst in the wetted state the reverse will occur and the hydrophilic groups will orientate themselves towards the aqueous/gel interface.

Any surface with an absorbed layer of surfactant material, where the surfactant possesses a shell of water molecules associated with its exposed head groups will not be subject to same levels of surface mobility and will thereby exhibit a reduced hysteresis. Any treated material that shows a low advancing contact angle combined with a negligible hysteresis could be considered to be fully wettable and is taken as the gold standard in these studies.

The DCA experiments were carried out in two parts. Initial studies were carried out on a series of pre-made flat sheets of hydrogel based on the range of monomers used in commercial lens materials synthesized from HEMA, HEMA/NVP and NVP/MMA/MA, as representatives of the materials used in FDA Group I, II & IV lenses. Each measurement was repeated five times on three separate samples of test hydrogel material. This procedure was repeated with actual examples of FDA Group I, II and IV contact lenses, using strips cut directly from Group I, II & IV lenses (SeeQuence®, Medalist® 66 & Surevue® lenses). The hydrogels materials and lenses tested are shown in Table 7 below.

TABLE 7

Hydrogel Materials and Lenses Tested by DCA

| Lens Type | FDA Category | Hydrogel Material | Test Lens |
|---|---|---|---|
| Low water content non-ionic | I | HEMA | SeeQuence ® Lens |
| High water content non-ionic | II | HEMA/NVP 80:20 | Medalist ® 66 Lens |
| High water content ionic | IV | NVP/MMA/MA 70:25:5 | Surevue ® Lens |

Each of the hydrogel samples and lenses were then soaked in the following surfactant solutions for at least one week: (1) 0.1 and 1.0% Tetronic (grade 1107), (2) 0.025% tyloxapol surfactant, and (3) 0.5% Pluronic (grade F127) surfactant. Tetronic® grade 1107 and Pluronic® grade F127 (Pluracare®, poloxamer 407) surfactants were supplied by BASF, while tyloxapol was sourced locally Sigma Chemical Co. Poole, Dorset, England.

Samples of the hydrogel materials approximately 20 mm long and 5 mm wide were cut to a uniform size using a sample cutter (Ray Ran, Nuneaton, England). One end of the gel was secured to a clip and attached to the electrobalance. A similar procedure was adopted to smaller test strips of commercially available contact lens materials, with the addition of a lead weight and hook to maintain the lens strip in a straightened condition. The test solutions used for soaking were all made up with HPLC grade water (FSA—Loughborough, England).

Figure 5:
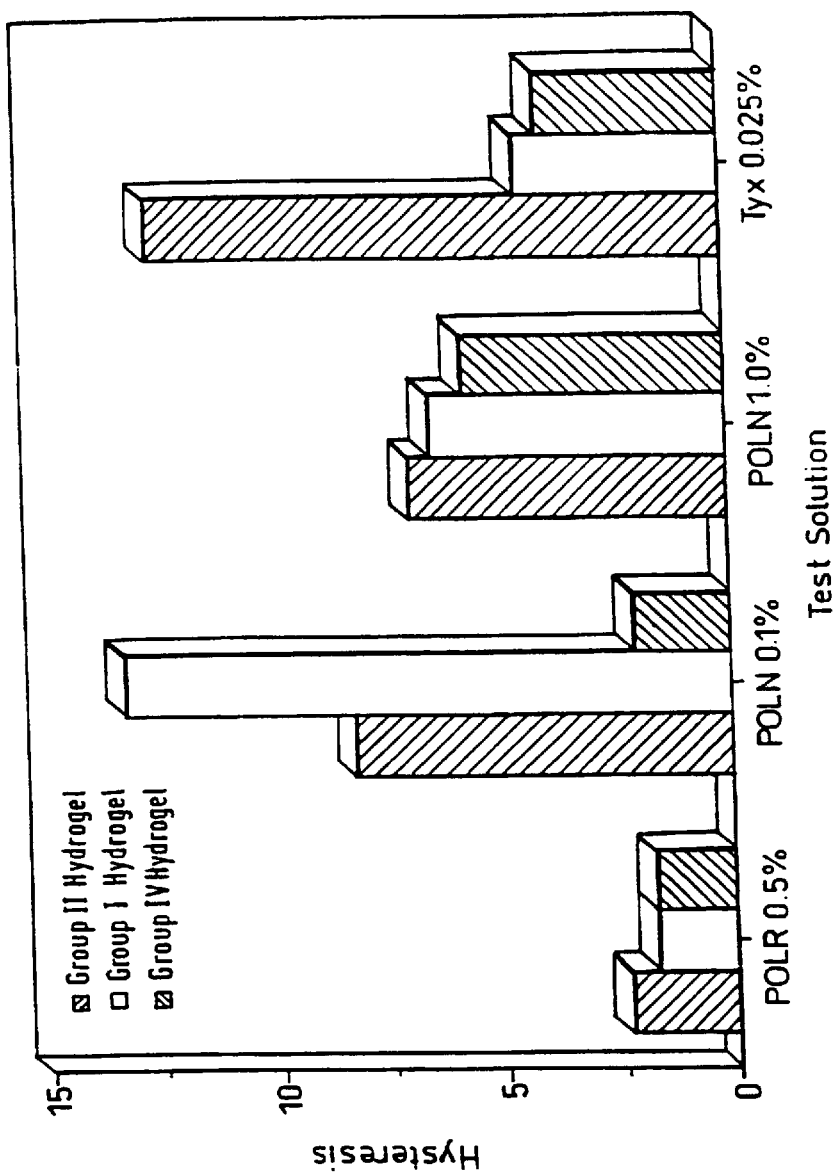
FIG. 5 shows the contact-angle hysteresis for various hydrogel materials soaked in poloxamer, poloxamine, and tyloxapol non-ionic surfactants.
Figure 6:
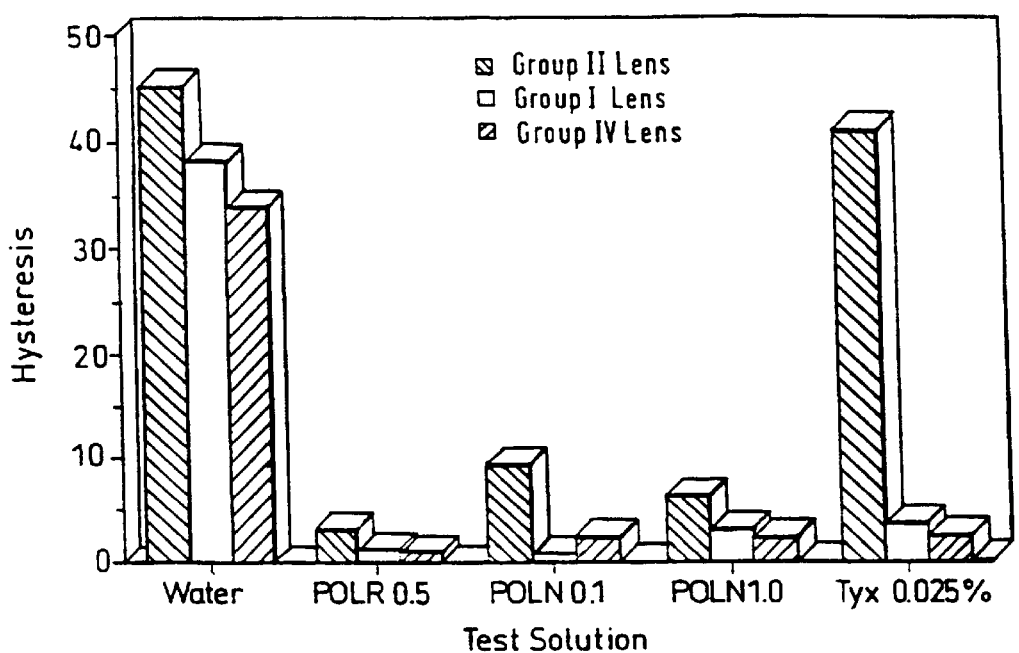
FIG. 6 shows the contact-angle hysteresis for Group I, II, and IV contact lenses soaked in poloxamer, poloxamine, and tyloxapol non-ionic surfactants.

As shown in FIG. 5, tyloxapol (Tyx), compared to the Pluronic® poloxamer (POLR) and the Tetronic® poloxamine (POLN) appears to be the least effective surfactant in wetting the hydrogel materials. Similarly, as shown in FIG. 6, tyloxapol was least effective in wetting the actual Group II lenses.

The persistence of the surface chemical effects were then investigated. It was considered that the presence of a positively charged ethylene diamine group at the center of the poloxamine molecule may enhance the adsorption of this surfactant onto the surfaces of anionic lenses (Group IV) via an electrostatic interaction. This effect was studied by comparing the persistence of the poloxamine with that obtained for the non-ionic surfactant tyloxapol. The influence of lens charge was observed by conducting the experiments at both low (pH 4) and neutral (pH 7).

The experiment was conducted by soaking samples of Group IV lenses in the following solutions for a period of four weeks: (a) 0.5% tyloxapol in HPLC grade water adjusted to pH 4, (b) 0.5% Tetronic® 1107 in HPLC grade water adjusted to pH 4, (c) 0.5% tyloxapol in HPLC grade water adjusted to pH 7, (d) 0.5% Tetronic® 1107 in HPLC grade water adjusted to pH 7. The pH values were not buffered but achieved by an initial addition of acid and the pH drift of the solutions was monitored during the four week experimental period and found to retain the initial pH value within 0.2 pH units which was adequate for these experiments.

Two samples, each from two separate lenses, were then taken from each solution, the excess surfactant shaken off and the advancing and receding contact angles assessed using DCA. Further lenses were removed from the test solutions, placed into plastic contact lens holders (Ciba Vision 10:10 contact lens baskets) and immersed in a glass powder jar (80 z) containing 300 mls of HPLC grade water. The lenses were then subjected to a process of vigorous controlled washing by constant stirring of the water with a Teflon® plastic magnetic bar. This procedure was continued for 30, 60, 120 and 240 minutes, respectively. At the end of each stirring period sample strips from two lenses were taken and contact angles assessed by DCA.

Figure 7:
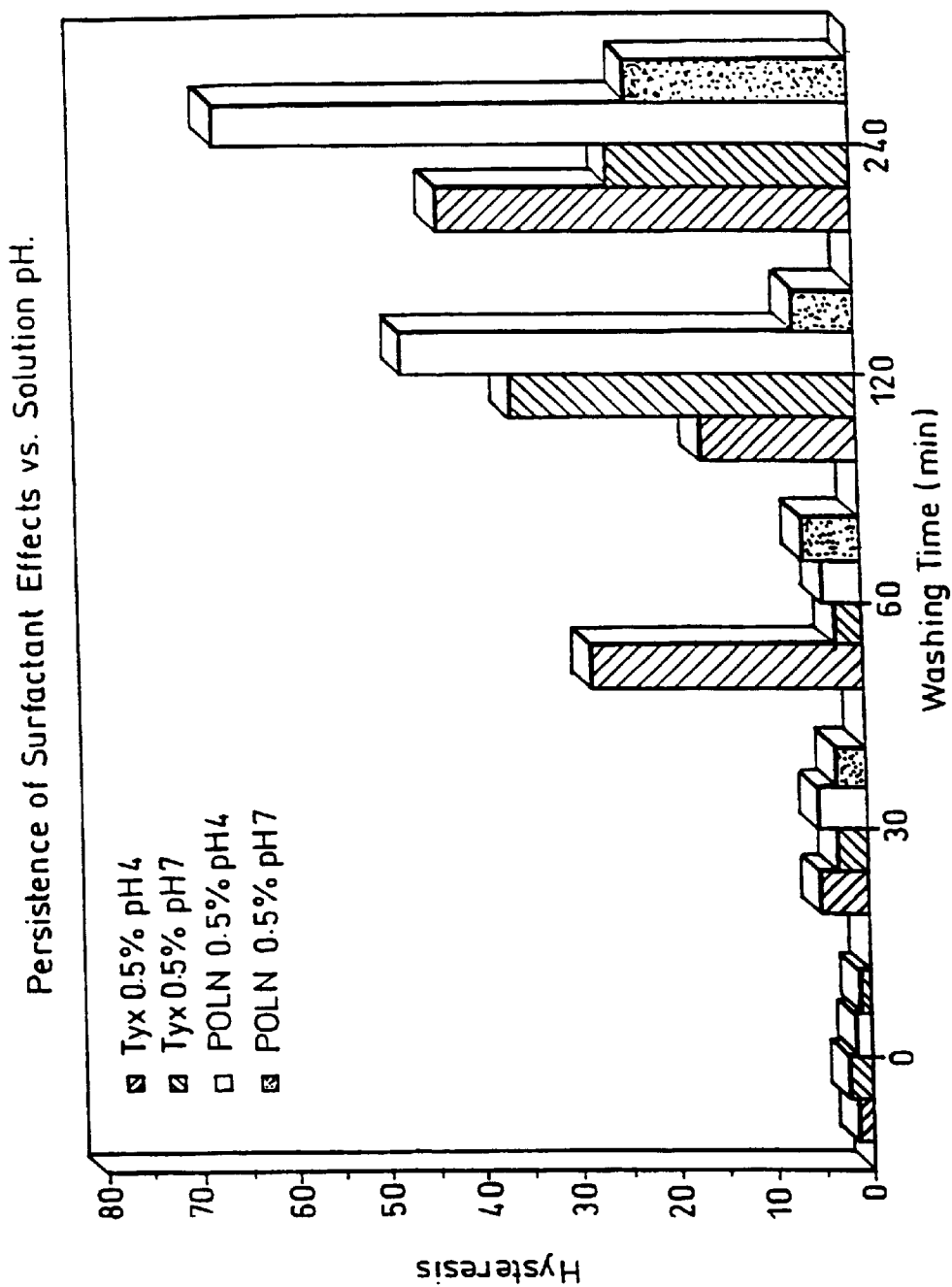
FIG. 7 shows the persistence of surfactant effects for poloxamine and tyloxapol surfactants.

The effects of a period of timed washing on Group IV lens hysteresis is graphically presented in FIG. 7. The most striking feature of this data is the rise in hysteresis with washing time, i.e. from 1.1 to 2.2 degrees after immediate removal from the surfactant solution, to 23.5 to 67.6 degrees after 240 minutes of controlled washing. The rate of increase in hysteresis is generally greater for both 0.5% tyloxapol and 0.5% poloxamine surfactant when the lenses are soaked in a surfactant solution adjusted to pH 4 rather than pH 7. Thus, the surfactant material is more readily removed when soaking is conducted at a lower pH. This is especially the case with the poloxamine which is more readily removed after 120 and 240 minutes of washing when soaked at the lower pH.

After soaking in solutions adjusted to pH 7, the reverse appears to be true where the poloxamine is less readily removed after 120 minutes of washing than tyloxapol, although after 240 minutes of washing the hysteresis for lenses treated with both surfactants is essentially equivalent. The differential effects of surfactant treatment at pH 4 and 7 probably arise from the reduced hydrogel pore size of the Group IV material at low pH as a consequence of the loss of charge and concomitant collapse of the polymer network. This, in turn, may prevent the incorporation of higher molecular weight surfactants such as poloxamine or poloxamer into the surface layers of the lens matrix and render the surfactant more prone to removal by washing. At pH 7, the expanded matrix may facilitate partial incorporation of the surfactant into the surface matrix and this may hinder removal of the surfactant molecules from the lens surface, thereby, retaining wettability of the latter.

While the invention has been described in conjunction with specific examples thereof, this is illustrative only. Accordingly, many alternatives, modifications, and variations will be apparent to those skilled in the art in light of the foregoing description and it is, therefore, intended to embrace all such alternatives, modifications, and variations as to fall within the spirit and scope of the appended claims.

We claim:

1. A method for packaging and storing a hydrogel contact lens comprising, prior to delivery of the contact lens to the customer-wearer, immersing the contact lens in an aqueous contact lens packing solution inside a package and heat sterilizing the solution, wherein the contact lens packing solution comprises a sterile ophthalmically safe aqueous solution comprising:
   a) from about 0.005 to about 2.0 weight percent of a non-ionic surfactant that is a compound comprising at least 90 weight percent of poly(oxyethylene) and poly(oxypropylene) segments, in one or more block copolymer chains, wherein the weight average molecular weight of said surfactant is from about 4000 to about 30,000 and wherein at least 40 percent of said segments are poly(oxyethylene) segments;
   b) an effective amount of a tonicity adjusting agent such that the solution has an osmolality of 200 to 400 mOsm/kg;
   wherein the solution has a pH of about 6 to 8 and does not contain an effective disinfecting amount of a disinfecting agent.

2. The method of claim 1, wherein the non-ionic surfactant is a poly(oxypropylene)-poly(oxyethylene) adduct of ethylene diamine.

3. The method of claim 1, wherein the solution further comprises a polymer selected from the group consisting of polyvinylalcohol, cellulose-derived polymers, and povidone.

4. The method of claim 1, wherein the solution further comprises an ionic or amphoteric surfactant for preventing folding or sticking of the lens.

5. The method of claim 1, wherein the solution further comprises a buffering agent.

6. The method of claim 5, wherein the buffering agent comprises a borate or phosphate compound.

7. The method of claim 1, further comprising hermetically sealing the contact lens and the contact lens packing solution in the package.

8. The method of claim 7, wherein heat sterilization is performed prior to sealing of the package.

9. The method of claim 7, wherein heat sterilization is performed subsequent to sealing of the package.

10. A method for packaging and storing a hydrogel contact lens, comprising immersing the contact lens in a sterile ophthalmically safe aqueous solution and heat sterilizing the solution, said solution comprising from about 0.005 to about 2.0 weight percent of a non-ionic surfactant that is a compound comprising at least 90 weight percent of poly(oxyethylene) and poly(oxypropylene) segments, in one or more block copolymer chains, wherein the weight average molecular weight of said surfactant is from about 4000 to about 30,000 and wherein at least 40 percent of said segments are poly(oxyethylene) segments;
   wherein the solution has a pH of about 6 to 8 and an osmolality of 200 to 400 mOsm/kg, and contains no germicide compound.

11. The method of claim 10, wherein the non-ionic surfactant is a poly(oxypropylene)-poly(oxyethylene) adduct of ethylene diamine.

12. A system for the storage and delivery of a hydrogel contact lens comprising a sealed container containing one or more unused hydrogel contact lens immersed in an aqueous contact lens packing solution, wherein the packing solution comprises:
   a) from about 0.005 to about 2.0 weight percent of a non-ionic surfactant that is a compound comprising at least 90 weight percent of poly(oxyethylene) and poly(oxypropylene) segments, in one or more block copolymer chains, wherein the weight average molecular weight of said surfactant is from about 4000 to about 30,000 and wherein at least 40 percent of said segments are poly(oxyethylene) segments;
   b) an effective amount of a tonicity adjusting agent such that the solution has an osmolality of 200 to 400 mOsm/kg;
   wherein the solution has a pH of about 6 to 8 and is heat sterilized and lacks an effective disinfecting amount of a disinfecting agent.

13. The system of claim 12, wherein the non-ionic surfactant is a poly(oxypropylene)-poly(oxyethylene) adduct of ethylene diamine.

14. A system for the storage and delivery of a hydrogel contact lens comprising a sealed container containing a hydrogel contact lens immersed in an aqueous contact lens packing solution, wherein the packing solution comprises from about 0.005 to about 2.0 weight percent of a non-ionic surfactant that is a compound comprising at least 90 weight percent of poly(oxyethylene) and poly(oxypropylene) segments, in one or more block copolymer chains, wherein the weight average molecular weight of said surfactant is from about 4000 to about 30,000 and wherein at least 40 percent of said segments are poly(oxyethylene) segments;
   wherein the solution has a pH of about 6 to 8 and an osmolality of 200 to 400 mOsm/kg, and is heat sterilized and lacks a germicide compound.

15. The system of claim 14, wherein the non-ionic surfactant is a poly(oxypropylene)-poly(oxyethylene) adduct of ethylene diamine.

16. A method for packaging and storing a hydrogel contact lens, comprising immersing the contact lens in a sterile ophthalmically safe aqueous solution and heat sterilizing the solution, said solution comprising from about 0.005 to about 5.0 weight percent of a non-ionic surfactant that is a compound comprising at least 90 weight percent of poly(oxyethylene) and poly(oxypropylene) segments, in one or more block copolymer chains, wherein the weight average molecular weight of said surfactant is from about 4000 to about 30,000 and wherein at least 40 percent of said segments are poly(oxyethylene) segments;
   wherein the solution has a pH of about 6 to 8 and an osmolality of 200 to 400 mOsm/kg, and contains no germicide compound.

17. A system for the storage and delivery of a hydrogel contact lens comprising a sealed container containing one or more unused hydrogel contact lens immersed in an aqueous contact lens packing solution, wherein the packing solution comprises:
   a) from about 0.005 to about 5.0 weight percent of a non-ionic surfactant that is a compound comprising at least 90 weight percent of poly(oxyethylene) and poly(oxypropylene) segments, in one or more block copolymer chains, wherein the weight average molecular weight of said surfactant is from about 4000 to about 30,000 and wherein at least 40 percent of said segments are poly(oxyethylene) segments;
   b) an effective amount of a tonicity adjusting agent such that the solution has an osmolality of 200 to 400 mOsm/kg;
   wherein the solution has a pH of about 6 to 8 and is heat sterilized and lacks an effective disinfecting amount of a disinfecting agent.

* * * * *